United States Patent [19]
Emery et al.

[11] Patent Number: 5,501,947
[45] Date of Patent: Mar. 26, 1996

[54] PCR DIAGNOSIS OF HUMAN PAPILLOMA VIRUS TYPE 16

[75] Inventors: Vincent C. Emery, Hampstead; Peggy J. Bavin, London; Patrick Walker, Hampstead, all of England

[73] Assignee: Royal Free Hospital School of Medicine, London, England

[21] Appl. No.: 965,274

[22] PCT Filed: Jul. 19, 1991

[86] PCT No.: PCT/GB91/01212

§ 371 Date: Mar. 12, 1993

§ 102(e) Date: Mar. 12, 1993

[87] PCT Pub. No.: WO92/01815

PCT Pub. Date: Feb. 6, 1992

[30] Foreign Application Priority Data

Jul. 19, 1990 [GB] United Kingdom ............ 9015845

[51] Int. Cl.$^6$ .............. C07H 21/00; C12Q 1/68; C12Q 1/70; C12P 19/34
[52] U.S. Cl. .............. 435/5; 435/6; 435/91.2; 536/24.33
[58] Field of Search .............. 435/5, 6, 91.2; 536/24.33

[56] References Cited

FOREIGN PATENT DOCUMENTS

| | | | |
|---|---|---|---|
| 0104217 | 4/1984 | European Pat. Off. | C12N 15/00 |
| 0301968 | 2/1989 | European Pat. Off. | C12A 1/70 |
| 0334694 | 9/1989 | European Pat. Off. | C12Q 1/68 |
| 0373352 | 6/1990 | European Pat. Off. | C12Q 1/70 |
| 0402132 | 12/1990 | European Pat. Off. | C12Q 1/68 |
| WO86/06816 | 10/1986 | WIPO | C12Q 1/68 |
| WO88/06634 | 9/1988 | WIPO | C12Q 1/70 |
| WO90/02821 | 3/1990 | WIPO | C12Q 1/70 |
| WO91/00868 | 1/1991 | WIPO | C07H 21/00 |

OTHER PUBLICATIONS

Stratagene Catalog 1988 (p. 39).
European Patent 373352 (Behring Werke AG) published Jun. 20, 1990 Detection of human papilloma virus–by DNA amplification and analysis (English Abstract).
Seedorf et al. Human Papillomavirus Type 16 DNA Sequence, Virology (1985) 145: 181–185.
Gen Bank Loci PPH16 (citing Seedorf et al.), PPH33CG (Feb. 16, 1987), and PPH31A (Dec. 15, 1989) Fast DB Search and Gen Align Alignment.
Maitland, et al., *Detection of human papillomavirus genes in human oral tissue biopsies and cultures by a polymerase chain reaction*, (1989) Chem. Abs. 11:192.
Wagatsuma, et al., *Analysis of integrated human papillomavirus type 16 DNA in cervical cancers; amplification of viral sequences together with cellular flanking sequences*, (1990) Chem. Abs. 112:195.

Primary Examiner—W. Gary Jones
Assistant Examiner—David Schreiber
Attorney, Agent, or Firm—Reed & Robins

[57] ABSTRACT

The invention provides oligonucleotides (A): and (B): and their derivatives. These oligos may be used as a pair of primers for the detection of HPV16 (SEQ ID NO:3) DNA in a sample, without false positives arising due to the presence of other HPV strains. Kits containing the primers and the use of the primers to screen populations are provided.

19 Claims, 3 Drawing Sheets

CERVICAL SMEAR SAMPLES AMPLIFIED WITH PV 16 PRIMERS 1 2 3 4 5 6 7 8 9 10 11 12 13 14 15 - - +

◁1746
◁1434

◁303
◁222

SOUTHERN BLOT OF PCR AMPLIFIED CERVICAL SMEAR
SAMPLES PROBED FOR HPV 16

Sequence of HPV 16 Nucleotides 1 – 1000
EMBL database entry: PA16

*PRIOR ART*

| | | | | | |
|---|---|---|---|---|---|
| ACTACAATAA | TTCATGTATA | AAACTAAGGG | CGTAACCGAA | ATCGGTTGAA | CCGAAACCGG |
| 10 | 20 | 30 | 40 | 50 | 60 |
| TTAGTATAAA | AGCAGACATT | TTATGCACCA | AAAGAGAACT | GCAATGTTTC | AGGACCCACA |
| 70 | 80 | 90 | 100 | 110 | 120 |
| GGAGCGACCC | AGAAAGTTAC | CACAGTTATG | CACAGAGCTG | CAAACAACTA | TACATGATAT |
| 130 | 140 | 150 | 160 | 170 | 180 |
| AATATTAGAA | TGTGTGTACT | GCAAGCAACA | GTTACTGCGA | CGTGAGGTAT | ATGACTTTGC |
| 190 | 200 | 210 | 220 | 230 | 240 |
| TTTTCGGGAT | TTATGCATAG | TATATAGAGA | TGGGAATCCA | TATGCTGTAT | GTGATAAATG |
| 250 | 260 | 270 | 280 | 290 | 300 |
| TTTAAAGTTT | TATTCTAAAA | TTAGTGAGTA | TAGACATTAT | TGTTATAGTT | TGTATGGAAC |
| 310 | 320 | 330 | 340 | 350 | 360 |
| AACATTAGAA | CAGCAATACA | ACAAACCGTT | GTGTGATTTG | TTAATTAGGT | GTATTAACTG |
| 370 | 380 | 390 | 400 | 410 | 420 |
| TCAAAAGCCA | CTGTGTCCTG | AAGAAAAGCA | AAGACATCTG | GACAAAAAGC | AAAGATTCCA |
| 430 | 440 | 450 | 460 | 470 | 480 |
| TAATATAAGG | GGTCGGTGGA | CCGGTCGATG | TATGTCTTGT | TGCAGATCAT | CAAGAACACG |
| 490 | 500 | 510 | 520 | 530 | 540 |
| TAGAGAAACC | CAGCTGTAAT | CATGCATGGA | GATACACCTA | CATTGCATGA | ATATATGTTA |
| 550 | 560 | 570 | 580 | 590 | 600 |
| GATTTGCAAC | CAGAGACAAC | TGATCTCTAC | TGTTATGAGC | AATTAAATGA | CAGCTCAGAG |
| 610 | 620 | 630 | 640 | 650 | 660 |
| GAGGAGGATG | AAATAGATGG | TCCAGCTGGA | CAAGCAGAAC | CGGACAGAGC | CCATTACAAT |
| 670 | 680 | 690 | 700 | 710 | 720 |
| ATTGTAACCT | TTTGTTGCAA | GTGTGACTCT | ACGCTTCGGT | TGTGCGTACA | AAGCACACAC |
| 730 | 740 | 750 | 760 | 770 | 780 |
| GTAGACATTC | GTACTTTGGA | AGACCTGTTA | ATGGGCACAC | TAGGAATTGT | GTGCCCCATC |
| 790 | 800 | 810 | 820 | 830 | 840 |
| TGTTCTCAGA | AACCATAATC | TACCATGGCT | GATCCTGCAG | GTACCAATGG | GGAAGAGGGT |
| 850 | 860 | 870 | 880 | 890 | 900 |
| ACGGGATGTA | ATGGATGGTT | TTATGTAGAG | GCTGTAGTGG | AAAAAAAAAC | AGGGGATGCT |
| 910 | 920 | 930 | 940 | 950 | 960 |
| ATATCAGATG | ACGAGAACGA | AAATGACAGT | GATACAGGTG | | |
| 970 | 980 | 990 | 1000 | | |

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGGGTCGGTG GACCGGTCGA TGTA                                      24
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GGGCTCTGTC CGGTTCTGCT TGTC                                      24
```

( 2 ) INFORMATION FOR SEQ ID NO:3:

( i ) SEQUENCE CHARACTERISTICS:
        ( A ) LENGTH: 1000 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ACTACAATAA  TTCATGTATA  AAACTAAGGG  CGTAACCGAA  ATCGGTTGAA  CCGAAACCGG    60
TTAGTATAAA  AGCAGACATT  TTATGCACCA  AAAGAGAACT  GCAATGTTTC  AGGACCCACA   120
GGAGCGACCC  AGAAAGTTAC  CACAGTTATG  CACAGAGCTG  CAAACAACTA  TACATGATAT   180
AATATTAGAA  TGTGTGTACT  GCAAGCAACA  GTTACTGCGA  CGTGAGGTAT  ATGACTTTGC   240
TTTTCGGGAT  TTATGCATAG  TATATAGAGA  TGGGAATCCA  TATGCTGTAT  GTGATAAATG   300
```

| | | | | | | |
|---|---|---|---|---|---|---|
| TTTAAAGTTT | TATTCTAAAA | TTAGTGAGTA | TAGACATTAT | TGTTATAGTT | TGTATGGAAC | 360 |
| AACATTAGAA | CAGCAATACA | ACAAACCGTT | GTGTGATTTG | TTAATTAGGT | GTATTAACTG | 420 |
| TCAAAAGCCA | CTGTGTCCTG | AAGAAAAGCA | AAGACATCTG | GACAAAAAGC | AAAGATTCCA | 480 |
| TAATATAAGG | GGTCGGTGGA | CCGGTCGATG | TATGTCTTGT | TGCAGATCAT | CAAGAACACG | 540 |
| TAGAGAAACC | CAGCTGTAAT | CATGCATGGA | GATACACCTA | CATTGCATGA | ATATATGTTA | 600 |
| GATTTGCAAC | CAGAGACAAC | TGATCTCTAC | TGTTATGAGC | AATTAAATGA | CAGCTCAGAG | 660 |
| GAGGAGGATG | AAATAGATGG | TCCAGCTGGA | CAAGCAGAAC | CGGACAGAGC | CCATTACAAT | 720 |
| ATTGTAACCT | TTTGTTGCAA | GTGTGACTCT | ACGCTTCGGT | TGTGCGTACA | AAGCACACAC | 780 |
| GTAGACATTC | GTACTTTGGA | AGACCTGTTA | ATGGGCACAC | TAGGAATTGT | GTGCCCATC | 840 |
| TGTTCTCAGA | AACCATAATC | TACCATGGCT | GATCCTGCAG | GTACCAATGG | GGAAGAGGGT | 900 |
| ACGGGATGTA | ATGGATGGTT | TTATGTAGAG | GCTGTAGTGG | AAAAAAAAAC | AGGGGATGCT | 960 |
| ATATCAGATG | AGCAGAACGA | AAATGACAGT | GATACAGGTG | | | 1000 |

PCR DIAGNOSIS OF HUMAN PAPILLOMA VIRUS TYPE 16

CROSS-REFERENCE TO RELATED APPLICATIONS

This application originates from International Application No. PCT/GB91/01212, filed Jul. 19, 1991, based on United Kingdom Application No. 901584.2, filed Jul. 19, 1990.

FIELD OF THE INVENTION

This invention relates to an improved method of detection of human papillomavirus (HPV), in particular HPV using the polymerase chain reaction (PCR).

BACKGROUND OF THE INVENTION

Papillomaviruses are a group of closely related viruses that produce a spectrum of diseases in Man and other mammals. At present there are in excess of 57 different types of human papillomaviruses. The definition of a new type is that it possesses less than 50% cross hybridisation with the DNA of known species in the liquid phase according to a standard protocol. A number of human diseases have been attributed to specific papillomavirus types; for example, plantar warts—papillomavirus type 1 and common warts—papillomavirus type 7.

Human papilloma viruses have also been implicated in the development of cervical cancer (zur Eausen, 1977). This was based on observations that HPV infection was present in a high percentage of patients with cervical intraepithelial neoplasia (CIN) and invasive carcinoma of the cervix (Walker et al, 1983). The availability of cloned DNA for specific HPV types has allowed the prevalence of HPV infection in disease tissue to be assessed using a range of hybridization studies. These studies have shown that between 60 and 90% of significant CIN lesions and invasive cancers contained HPV DNA sequences whereas the prevalence of HPV DNA amongst normal controls was between 9 and 23%. Molecular analysis has shown that certain types of HPV, such as HPV 16, 31, 33 and 35 are more strongly associated with malignant changes of the cervix and are able to immortalise primary human keratinocytes and transform established cell lines. Other types of HPV such as HPV 6 and 11 are associated with benign lesions and condyloma acuminata. These data support the hypothesis that HPV infection, in particular HPV 16, is indeed a causal or contributory agent to squamous cancer.

PCR (Saiki et al, 1988) is based on the enzymic amplification of a DNA target fragment by the use of two oligonucleotide primers that hybridise to opposite strands of the target sequence. The primers are oriented such that their 3' termini oppose each other.

Two recent studies (Young et al, 1989, Tidy et al, 1989) have used PCR to amplify specific HPV sequences from cervical tissue. Under the conditions used by these workers it has been shown that, in contrast to other hybridisation studies, that positive signals obtained for HPV types in the normal population is between 70–84%. Recently one study (Tidy et al, 1989) has been retracted in part (Tidy and Farrell, 1989) thus highlighting the problems associated with using PCR to identify the presence of HPV in the cervix.

Tidy et al amplified sequences within the upstream regulatory region (between nucleotides 7765 and 7775), whilst Young et al used oligonucleotide primers to amplify a region from nucleotides 421 to 540 within the E6 gene.

The prevalences of HPV 16 infection reported in these studies are surprisingly high when compared with data from Southern blot, filter in-situ hybridization, dot-blot studies and certain PCR studies (Van der Brule, 1989). The high prevalence identified in these PCR studies may be accounted for by the inability of the oligonucleotide primers to exhibit specificity for the target DNA sequence of interest and hence yielding an amplified DNA fragment for other papillomavirus types present in the sample.

A fundamental requirement for the PCR reaction is the availability of oligonucleotide primers that are specific for the DNA sequence to which they are complementary and which enable efficient amplification of target sequences. By "specific", it is meant that the sequences of the oligonucleotides are such that they do not hybridize to a significant degree to any DNA sequences present in the sample which is being analyzed by a PCR reaction other than one or other of the ends of the target sequence.

Following extensive computer homology and alignment searches which compared HPV 16 DNA sequences with other closely related papillomavirus types, in particular, types 6, 11, 18 and 31, we have identified regions of the HPV 16 genome which are unique to this type of papilloma virus.

These regions provide suitable targets for use in the present invention.

It is known that HPV 16 DNA is integrated into the host cell DNA in significant cervical disease in such a way that only the E6 and E7 genes are transcribed. Integration occurs so as to disrupt the open reading frames E1 and E2. Using this information we have chosen two primers that hybridise to a distal region of the E6 gene and the proximal region of the E7 gene of HPV 16. The distance between the translational stop codon of the E6 gene and the methionine initiation codon of the E7 protein is 2 nucleotides in HPV 16 whereas in the closely related HPV 6 and 11 the termination codon of the E6 protein overlaps with the methionine initiation codon of the E7 protein by 24 nucleotides, thus any mismatch priming between the primers and HPV 6 and 11 will be immediately visible due to the different sizes of the amplimers. Hence oligonucleotides hybridising to this region can be utilised to specifically identify the amplified region of HPV 16 target DNA.

DESCRIPTION OF THE INVENTION

The present invention thus provides oligonucleotide A:

5' GGGGTCGGTGGACCGGTCGATGTA 3' (SEQ ID NO:1) and derivatives thereof.

The present invention also provides oligonucleotide B:

5' GGGCTCTGTCCGGTTCTGCTTGTC 3' (SEQ ID NO:2) and derivatives thereof.

The full length sequences A (SEQ ID NO:1) and B (SEQ ID NO:2) hybridise to the HPV 16 genome at positions 489–512 and 689–712 respectively.

Derivatives of A (SEQ ID NO:1) and B (SEQ ID NO:2) include fragments of A and B of at least 10 nucleotides in length, and oligonucleotides which comprise such fragments. Oligonucleotides which comprise such fragments will be of a size suitable for use as a PCR primer, eg from 10 to 40, preferably 12 to 24 nucleotides in length, Desirably, such oligonucteotides will be derived from the native HPV 16 sequence flanking the regions from which A (SEQ ID NO:1) and B (SEQ ID NO:2) are derived. Typically such oligonucleotides will be derived from positions 477 to 524 for A (SEQ ID NO:1) and 677 to 724 for B (SEQ ID NO:2).

Fragments of A (SEQ ID NO:1) and B (SEQ ID NO:2) of at least 10, eg. 12, 15, 18 or 21 nucleotides in length will correspond to contiguous sequences derived from the 24-nucleotide-length sequences A (SEQ. ID NO:1) and B (SEQ ID NO:2). Preferably, fragments and oligonucleotides comprising such fragments of A (SEQ ID NO:1) and B (SEQ ID NO:2) will have a high GC content, eg. more than 50%.

Unless specified to the contrary, references hereafter to oligonucleotides A (SEQ ID NO:1) and B (SEQ ID NO:2) also includes derivatives of A (SEQ ID NO:1) and B (SEQ ID NO:2) as defined above.

The present invention also provides oligonucleotides A (SEQ ID NO:1) and B (SEQ ID NO:2) for use as a pair of PCR primers for the detection of the presence of HPV 16 DNA in a sample.

The present invention further provides an improved method for detecting the presence of HPV 16 DNA in a sample which comprises preparing oligonucleotides A (SEQ ID NO:1) and B (SEQ ID NO:2) as defined above specific for HPV 16 and using these oligonucleotides to detect HPV 16 DNA in the sample using a polymerase chain reaction (PCR).

The oligonucleotides of the present invention may be used under standard PCR conditions (Saiki et al, 1988). The sample of DNA to be analyzed is added to the reaction mixture, along with oligonucleotides A (SEQ ID NO:1) and B (SEQ ID NO:2), heated to denature the DNA in the sample, cooled to allow the oligonucleotides A (SEQ ID NO:1) and B (SEQ ID NO:2) to anneal to their target sequences, and the PCR reaction started by adding a DNA polymerase, eg. Taq polymerase. Repeated cycles eg. 20 to 40 cycles of heating and annealing, and if required, the addition of fresh polymerase during each cycle, results in the amplification of the target DNA. Typically, in each cycle, the mixture is heated to about 95° C. over about 1 minute, annealed for 1–3 minutes at about 40° C., and reacted at about 72° C. for 1–2 minutes.

Generally the PCR buffer comprises 10–50 mM, preferably 20–30 mM Tris-HCl, 10–25 mM preferably 15–20 mM ammonium sulphate, 1–10 mM preferably 2–5 mM magnesium chloride, 5–15 mM eg. 8–12 mM 2-mercaptoethanol, 0.001–0.004% gelatin, 100–300 mM of each deoxynucleotide triphosphate (dATP, dCTP, dGTP and dTTP). Desirably, less than 15µM, eg. 1–10 or 1–5µM (final concentration) of primers A (SEQ ID NO:1) and B (SEQ ID NO:2) are used (advantageously in equimolar amounts) in the reaction, and 0.5 to 5 units of Taq polymerase are used to start the reaction.

The PCR reaction is preferably performed by denaturation at 90°–98° C. for 1 to 10 minutes, followed by 20 to 40, eg. 30 to 35 cycles of amplification, one cycle representing denaturation at 90°–98° C. for 1 to 3 minutes, primer annealing at 50° to 70° C. for 1 to 3 minutes, and DNA polymerization at 60° to 80° C. for 1 to 4 minutes.

The oligonucleotides of the present invention are most preferably used under the following conditions: The reaction buffer is: 25 mM Tris-HCl pH 8.4 17 mM ammonium sulphate, 3 mM magnesium chloride, 10 mM 2-mercaptoethanol, 0.002% gelatin, 1 µM HPV 16 primers, 1 unit of Taq polymerase, 200 µM of each deoxynucleotide triphosphate (deoxyadenosine-, deoxycytidine-, deoxyguanosine- and deoxythymidine triphosphate). The PCR is optionally performed as follows:

denaturation at 95° C. for 6 minutes, then 35 cycles of amplication, one cycle represents denaturation at 94° C. for 1 minute 30 seconds, primer annealing at 60° C. for 1 minute 30 seconds and DNA polymerisation at 72° C. for 2 minutes. After the 35th cycle the samples are preferably incubated at 72° C. for a further 10 minutes.

The above reaction differs from the procedures detailed by Saiki et al (1988) in the use of 3 mM magnesium chloride and the presence of each primer at a concentration of 1 µM final concentration in the Taq buffer mixture and use of an annealing temperature of 60° C. These modifications produce enhanced fidelity of reaction with primers HPV 16 A (SEQ. ID NO:1) and B (SEQ. ID NO:2).

DESCRIPTION OF THE DRAWINGS

FIG. 5 shows the sequence of nucleotides 1 to 1000 of HPV16. The sequence illustrated is the EMBL database entry PA16 (SEQ. ID NO:3).

As will be illustrated in the Examples which follow, diagnosis of HPV 16 using primers A and B indicates that the prevalence of HPV 16 is lower than that determined by others eg. Young et al, and 1989 Tidy et al, 1989. This is because the higher degree of specificity of our primers results in far fewer false positive than previously achievable whilst accurately identifying all samples that contain at least five HPV 16 genome equivalents.

The utility of the diagnostic method described in this invention to detect HPV 16 DNA in DNA extracted from cervical smears from a general population sample expected to be "normal" with respect to their cervical pathology and a subset of these same women who were identified as having significant cervical disease is described in Examples 1 and 2 respectively. Utilising oligonucleotides A (SEQ ID NO:1) and B (SEQ ID NO:2) in a PCR reaction we show that HPV 16 prevalence in the general population is lower than that determined by other PCR based studies and is likely to be 18.9%. Furthermore, as Example 2 indicates, the detection of HPV 16 in cervical smears using our primer pairs appears to correlate with disease status. Hence the present invention may be used as a diagnostic method for identifying patients with significant cervical disease when used in conjunction with existing methods such as cytology and may also be utilised in discriminating patients at a higher risk of progressing to cervical cancer.

EXAMPLE 1

Between May and September 1987, a cervical screening service, combining cytology and colposcopy, was offered to all adult female patients of a General Practice on the borders of London and Hertfordshire, irrespective of when they had their last cervical smear. The practice was in a predominantly middle class area. 249 women volunteered for this service from a total of 2879 female patients over the age of 21.

The 249 women in the study group were examined by cytology, colposcopy and histological analysis of directed biopsies when appropriate, as described by Giles et al (1988). For each patient two cervical smears were taken; one for standard cytological analysis and the second placed in 10 mls of cold phosphate buffered saline to be used for the subsequent virological analysis. These cells were collected by centrifugation and the DNA extracted with SDS-proteinase K lysis and phenol/chloroform purification followed by ethanol precipitation as described in Sambrook et al (1989).

Figure 1:
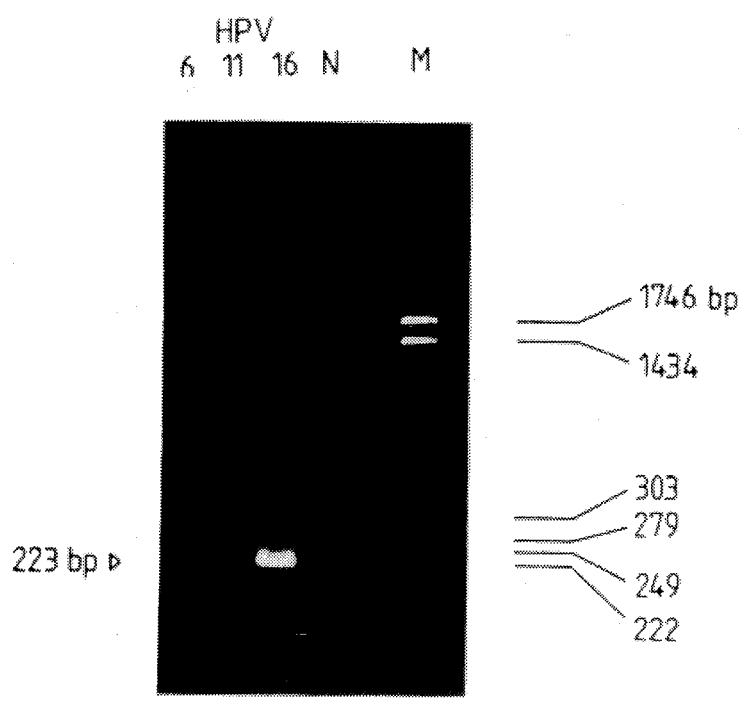
FIG. 1 shows the identification of HPV 16 DNA in the presence of heterologous DNA and DNA of other HPV types, using PCR with primers A (SEQ ID NO:1) and B (SEQ ID NO:2) as defined above. Under the optimum reaction conditions described above HPV 16 is amplified and no cross reaction leading to amplification of related papillomaviruses is seen.
Figure 2:
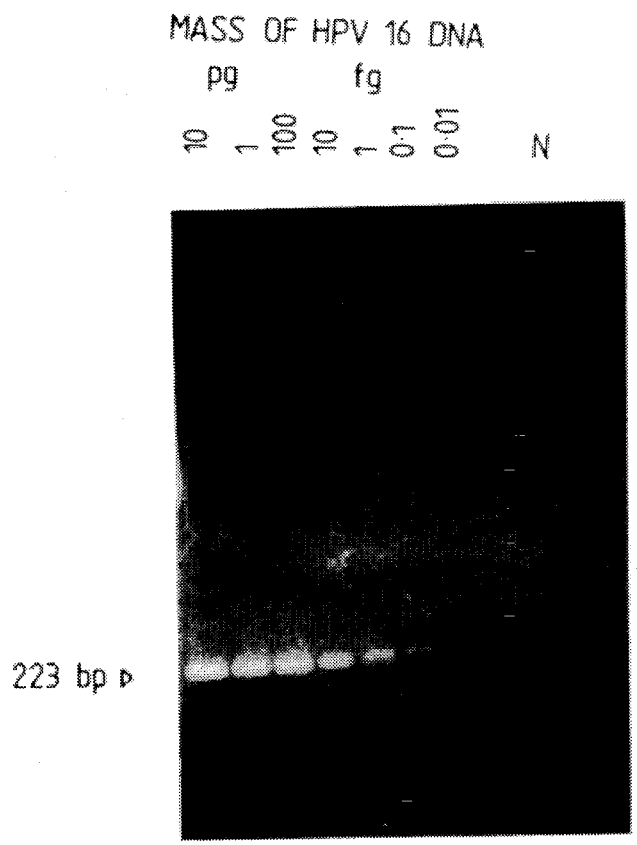
FIG. 2 demonstrates that the sensitivity of detection of HPV 16 was 5 genome equivalents. The maintenance of specificity without loss of sensitivity is an important facet of the conditions and primers described in this invention and are instrumental in the accurate detection of HPV 16 in cervical smears from normal and diseased women.
Figure 3:
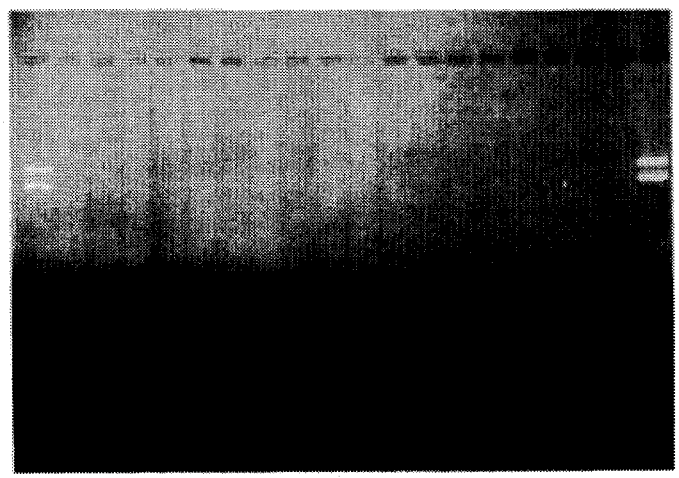
FIG. 3 depicts the result of PCR amplification of the cervical smears with HPV16 primers.
Figure 4:
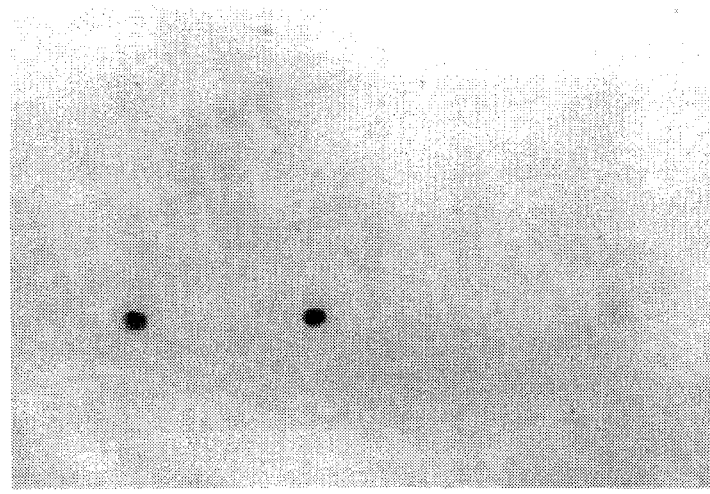
FIG. 4 depicts a Southern blot of the PCR amplified cervical smear samples probed for HPV16 using a target sequence-specific probe.

1 μg of the DNA isolated in this way was subjected to the PCR analysis. The PCR reaction buffer contained 25 mM Tris-HCl pH 8.4 17mM ammonium sulphate, 3 mM magnesium chloride, 10 mM 2-mercaptoethanol, 0.002% gelatin, 1 μM HPV 6 primers, 1 unit of Taq polymerase, 200 μM of each deoxynucleotide triphosphate (deoxyadenosine-, deoxycytidine-, deoxyguanosine- and deoxythymidine triphosphate). The PCR was performed by denaturation at 95° C. for 6 minutes, then 35 cycles of amplication, one cycle represents denaturation at 94° C. for 1 minute 30 seconds, primer annealing at 60° C. for 1 minute 30 seconds and DNA polymerisation at 72° C. for 2 minutes. The results obtained for 15 samples are shown in FIGS. 3 and 4. All samples were analyzed on two separate occasions using DNA extracted from coded cervical smear samples. Samples in which discrepant results were obtained were subjected to two further PCR analyses to exclude HPV 16 DNA contamination accounting for the original positive signal. In each analysis positive and negative controls, consisting of cloned HPV 16 DNA and water respectively, were included to verify the results and to avoid false positive signals due to contamination.

The cumulative analysis yielded a prevalence for HPV 16 within these women, of 18.9% (47/249).

EXAMPLE 2

Colposcopic examination of the 249 women studied in Example 1 showed that 29 women actually had cervical abnormalities and these could be stratified into the following grades of cervical disease.

|       |        |
|-------|--------|
| CIN 1 | n = 16 |
| CIN 2 | n = 8  |
| CIN 3 | n = 5  |

Using our PCR described in this application, the prevalence of HPV 16 in these patients was as follows:

| Grade of Disease | Number HPV Positive | Number of Patients | Percentage HPV Positive |
|---|---|---|---|
| CIN 3 | 4 | 5 | 80 |
| CIN 2 | 4 | 8 | 50 |
| CIN 1 | 2 | 16 | 12.5 |
| NORMAL | 37 | 220 | 16.8 |
| TOTAL | 47 | 249 | 18.9 |

Thus, using the procedures outlined above HPV 16 was detected in 4/5 women with significant cervical disease (CIN 3), 4/8 women with moderate disease (CIN 2) and 2/14 with mild/borderline disease (CIN 1). In those women with no cervical abnormalities 37/220 were HPV 16 positive yielding an HPV prevalence of 16.8% in the cytologically normal female population, Overall comparison of the HPV 16 status of women with significant disease (CIN 2 or 3) with those with mild or no disease demonstrated that HPV 16 is associated with cervical disease.

|  | CIN 2/3 | | Total Number |
|---|---|---|---|
| HPV 16 Status | NO | YES | in Group |
| Positive | 39 | 8 | 47 |
| Negative | 197 | 5 | 202 |
| TOTALS | 236 | 13 | 249 |

Fishers t test;
P = 0.001

These results can be used to produce an account of the sensitivity, specificity, positive predictive value and negative predictive value and relative risk as shown below:

| Parameter | Value |
|---|---|
| Sensitivity | 8/13 (0.62) |
| Specificity | 197/236 (0.83) |
| Positive Predictive value | 8/47 (0.17) |
| Negative Predictive value | 197/202 (0.98) |
| Relative risk | 6.9 |

The negative predictive value and specificity of this diagnostic test is high, but the positive predictive value of using HPV 16 alone to identify women with significant cervical disease is low i.e. many normal women have HPV 16 However, women who have significant cervical disease are 6.9 times more likely to have HPV 16 present in their smears.

On the basis of these data, the methodologies described in this invention have potential to identify women at risk of significant cervical disease and may be of prognostic value to identify women who will progress to cervical cancer.

EXAMPLE 3

The study group (Study group B) was composed of 200 patients sequentially attending the Royal Free Hospital colposcopy clinic, referred with a mildly abnormal cervical smear report. The clinical details of this population have been described in Giles et al (1988). A final diagnosis was not effected on twenty-one women in this group and these were excluded from the PCR analysis. The mean age for the population was 29 years (mean age of women with CIN: 26.9 years; mean age of women with normal cervical pathology: 33.5 years).

Two cervical scrapes were taken from each patient; one for standard cytological analysis and the second placed in 10 mls of cold phosphate buffered saline. The cells from the latter sample were pelleted by centrifugation and the DNA extracted with SDS-Proteinase K lysis and purified by phenol/chloroform extraction and ethanol precipitation.

The polymerase chain reaction (PCR) was performed as described in Example 1.

Statistical analysis of the distribution of results was determined using either $X^2$ or, where appropriate, Fishers exact test. The relative risk of having severe disease and HPV 16 was calculated by dividing the incidence rate of disease in the HPV 16 positive group by the incidence rate of disease in the HPV 16 negative group.

DISCUSSION OF EXAMPLES 1 TO 3

The PCR assay of the present invention was used to detect HPV 16 DNA in cervical scrape samples derived from 179 women referred to a colposcopy clinic with a smear suggesting minor grade disease. The overall prevalence of HPV 16in this study population is shown in Table 1. In addition the prevalence of HPV 16 in women in Example 1 (Study group A) is also shown. There was a significant difference in the prevalence of HPV 16 between the two study populations. HPV 16 was detected in 33 women from study A (18%) and 109 women from study B (61%; p< 0.0001).

Following colposcopic examination of all patients and histological examination of biopsy samples where appropriate, women with both study populations were assigned to the following groups: normal, wart virus infection (WV1) CIN 1, CIN 2 CIN 3. The HPV 16 prevalence in each of these groups within study. A (Example 1) and B (Example 3) is shown in Table 2. HPV 16 was more prevalent in patients with higher grade CIN especially CIN 3 in both studies (75% in study A vs 74.3% in study B). The prevalence of HPV 16 in both the CIN 2 and CIN 3 groups in each study population was not significantly different. However women with CIN 1 in study group B were more likely to be HPV 16 positive than women with CIN in study group A (p< 0.03). Furthermore, analysis of HPV 16 status of women with no evidence of cervical abnormality in both study populations reveals a significant difference between the two study populations (p<0.0001).

Comparison of HPV 16 prevalence in women who have never had cervical disease with those who have histologically proven cervical abnormalities is shown in Table 3. These data were produced by combining the two study populations and show that HPV 16 as more likely to be present in women with cervical disease (p<0.0001). When the women with abnormal cervical pathology were stratified according to minor grade (WVI and CIN 1) or major grade (CIN 2 and CIN 3) disease, the latter group were more likely to harbour HPV 16 (Table 4; p< 0.0002).

The relative risk associated with having HPV 16 and major grade cervical disease (CIN 2 and CIN 3) was calculated for both study populations and is shown in Table 5. In study A there is a relative risk of 5.68 associated with HPV 16 whereas in study B the relative risk is 1.48.

TABLE 1

Overall incidence of HPV 16 DNA in women attending a General Practice (Study A) and women referred to a colposcopy clinic with a smear suggesting mild dyskaryosis (Study B).

| Study population | Total | HPV 16 + ve (%) |
| --- | --- | --- |
| A | 183 | 33 (18) |
| B | 179 | 109 (61) |

$X^2 = 69.93$;
$p < 0.0001$

TABLE 2

Incidence of HPV 16 DNA in women with a final diagnosis of normal cervical pathology, wart virus infection (WVI), and CIN 1, CIN 2 and CIN 3 within study populations A and B. The statisical significance of differences between the two study populations in each group is also shown (n.s. = not significant).

| Final Diagnosis | Study A Total | Study A HPV 16 + ve (%) | Study B Total | Study B HPV 16 + ve (%) | Significance |
| --- | --- | --- | --- | --- | --- |
| Normal | 151 | 26 (17.2) | 54 | 34 (63) | p < 0.0001 |
| WVI | 10 | 0 (0) | 14 | 5 (35.6) | p < 0.003 |
| CIN 1 | 13 | 2 (15.4) | 45 | 24 (53.3) | p < 0.03 |
| CIN 2 | 5 | 2 (40) | 31 | 20 (64.5) | n.s. |
| CIN 3 | 4 | 3 (75) | 35 | 26 (74.3) | n.s. |

TABLE 3

Comparison of HPV 16 DNA prevalence in women with normal cervical pathology (ie. no history of cervical abnormality) and in women with any degree of abnormal cervical pathology. The abnormal cervical pathology group comprised women from Studies A and B.

| Cervical Pathology | Total | HPV 16 + ve (%) |
| --- | --- | --- |
| Normal | 151 | 26 (17.2) |
| Abnormal | 157 | 82 (52.2) |

$X^2 = 41.4$;
$p < 0.0001$

TABLE 4

Prevalence of HPV 16 DNA in women with minor grade cervical disease (CIN 1) and major grade cervical disease (CIN 2 and CIN 3). The analysis was performed on data obtained by combining the results of Studies A and B.

| Cervical disease status | Total | HPV 16 + ve (%) |
| --- | --- | --- |
| Minor grade | 82 | 31 (37.8) |
| Major grade | 75 | 51 (68) |

$X^2 = 14.3$;
$p < 0.0002$

TABLE 5

Relative risk of associated with the presence of HPV 16 DNA and major grade cervical disease for study populations A and B.

| Population | Relative risk of HPV 16 with CIN 2/3 (95% confidence limit) |
| --- | --- |
| Study A | 5.63 (1.61–20.02) |
| Study B | 1.48 (0.96–2.27) |

References van Brule, A J C, Claas E C J, du Maine Met al. (1989). Use of anticontamination primers in the polymerase chain reaction for the detection of human papillomavirus genotypes in cervical scrapes and biopsies. J. Med. Virol. 29, 20–27.

Giles J A, Hudson E, Crow J, Williams, D and Walker, P (1988). Colposcopic assessment of the accuracy of cervical cytology screening. British Medical Journal 296, i:311, 1099–1102.

Saiki R K, Golfand D H, Stoffel S, et al (1988) Primer directed enzymic amplification of DNA with a thermostable DNA polymerase.. Science 239, 487–491.

Sambrook J. et al (1989) Molecular Cloning: A Laboratory Manual. Cold Spring Harbour.

Tidy J A, Parry G C N, Ward Pet al (1989) High rate of Human Papillomavirus type 16 infection in cytologically normal cervices. Lancet i: 434.

Tidy J and Farrell P J (1989). Retraction: human paillomavirus subtype 16b. The Lancet ii, 1535.

Walker P et al (1983) The prevalence of Human papillomavirus antigen in patients with cervical intraepithelial neoplasia. Br. J. Cancer 48, 99-1-1.

Young L S, Revan I S, Johnson M A et al (1989) The polymerase chain reaction: a new epidemiological tool for investigating cervical human papillomavirus infection. Br. Med. J. 298, 14–18.

Zur Hausen H. (1977) Human papillomaviruses: a-possible role in sqamous cell carcinoma. Curr. Top. Microbiol. Immunol. 78,1.

---

We claim:

1. A method for detecting the presence of HPV 16 DNA in a DNA sample which comprises bringing the sample into contact with PCR primer oligonucleotide A:

5' GGGGTCGGTGGACCGGTCGATGTA 3' (SEQ ID NO:1) or a fragment of at least 15 contiguous nucleotides thereof, and PCR primer oligonucleotide B:

5' GGGCTCTGTCCGGTTCTGCTTGTC 3' (SEQ ID NO:2) or a fragment of at least 15 contiguous nucleotides thereof, treating the sample to denature the DNA, conducting a polymerase chain reaction, thereby amplifying the HPV 16 DNA, and detecting the amplified HPV 16 DNA.

2. A method according to claim 1 wherein the primers are oligonucleotides A:

5' GGGGTCGGTGGACCGGTCGATGTA 3' (SEQ ID NO:1) and B:

5' GGGCTCTGTCCGGTTCTGCTTGTC 3' (SEQ ID NO:2).

3. A method according to claim 1 wherein the primers are used in the PCR at a concentration of 1 μM.

4. A method according to claim 1 wherein the sample is a cervical smear.

5. A kit for the detection of the presence of HPV 16 [(SEQ ID NO:3)] DNA in a sample comprising a pair of PCR primers which are primer A:

5' GGGGTCGGTGGACCGGTCGATGTA 3' (SEQ ID NO:1) or a fragment of at least 15 contiguous nucleotides thereof, and primer B:

5' GGGCTCTGTCCGGTTCTGCTTGTC 3' (SEQ ID NO:2) or a fragment of at least 15 contiguous nucleotides thereof, optionally together with a buffer suitable for a PCR.

6. A kit according to claim 5 wherein the primers are A:

5" GGGGTCGGTGGACCGGTCGATGTA 3' (SEQ ID NO:1) and B:

5' GGGCTCTGTCCGGTTCTGCTTGTC 3' (SEQ ID NO:2).

7. Oligonucleotide A:

5' GGGGTCGGTGGACCGGTCGATGTA 3' (SEQ ID NO:1) or a fragment of at least 15 contiguous nucleotides thereof.

8. A method of screening a population for the presence of HPV 16 comprising analysing samples from the population by a method according to claim 1.

9. A method according to claim 8 wherein the population is an adult female population.

10. A method according to claim 2 wherein the primers are used in the PCR at a concentration of 1 μM.

11. A method according to claim 2 wherein the sample is a cervical smear.

12. A method according to claim 3 wherein the sample is a cervical smear.

13. A method of screening a population for the presence of HPV 16 comprising analysing samples from the population by a method according to claim 2.

14. A method of screening a population for the presence of HPV 16 comprising analysing samples from the population by a method according to claim 3.

15. A method of screening a population for the presence of HPV 16 comprising analysing samples from the population by a method according to claim 4.

16. A method of screening a population for the presence of HPV 16 comprising analysing samples from the population by a method according to claim 11.

17. A method of screening a population for the presence of HPV 16 comprising analysing samples from the population by a method according to claim 12.

18. A method of screening a population for the presence of HPV 16 comprising analysing samples from the population with a kit according to claim 5.

19. A method of screening a population for the presence of HPV 16 comprising analysing samples from the population with a kit according to claim 6.

* * * * *